United States Patent [19]

Albert et al.

[11] Patent Number: 4,655,075
[45] Date of Patent: Apr. 7, 1987

[54] VIBRATING TUBE DENSIMETER

[75] Inventors: Henry J. Albert, Bettendorf, Iowa; Robert H. Wood, Newark, Del.

[73] Assignee: University of Delaware, Newark, Del.

[21] Appl. No.: 830,436

[22] Filed: Feb. 19, 1986

Related U.S. Application Data

[63] Continuation-in-part of Ser. No. 654,443, Sep. 26, 1984.

[51] Int. Cl.⁴ .............................................. G01N 9/00
[52] U.S. Cl. ................................................... 73/32 A
[58] Field of Search ..................... 73/32 A, 32 R, 579, 73/583, 861.38, 861.37; 331/65, 116 M, 156

[56] References Cited

U.S. PATENT DOCUMENTS

| | | | |
|---|---|---|---|
| 3,117,440 | 1/1964 | Wilner | 73/32 A |
| 3,728,893 | 4/1973 | Janssen | 73/32 A |
| 4,187,721 | 2/1980 | Smith | 73/861.38 |
| 4,262,523 | 4/1981 | Stansfeld | 73/32 A |
| 4,422,338 | 12/1983 | Smith | 73/861.38 |
| 4,491,009 | 1/1985 | Ruesch | 73/32 A |
| 4,524,610 | 6/1985 | Fitzgerald et al. | 73/32 A |

Primary Examiner—Stewart J. Levy
Assistant Examiner—Robert R. Raevis
Attorney, Agent, or Firm—Dean R. Rexford

[57] ABSTRACT

A vibrating tube densimeter characterized by separate electrical conductors attached to and moving with the tube. By interaction with a constant magnetic field in which they move, and in cooperation with an electronic circuit outside the invention, one of the conductors vibrates the tube and the other senses the vibration. The novel design is simple and permits operation at high temperatures.

1 Claim, 3 Drawing Figures

VIBRATING TUBE DENSIMETER

The government has rights in this invention pursuant to Grant Number CHE8009672 awarded by the U.S. National Science Foundation.

This application is a continuation in part of our earlier application Ser. No. 06/654,443 filed 09/26/84.

BACKGROUND OF THE INVENTION AND PRIOR ART

This invention pertains to a vibrating tube densimeter for measuring the density of fluids, either batchwise or continuously.

The principle of the vibration densimeter lies in the observation that the square of the vibration period at resonant frequency, sometimes called the natural vibration period, is a linear function of the mass of the vibrating body.

The density of the test fluid can be derived from first principles, knowing the volume of the tube, but it is generally more practical to calibrate the device empiracally using one or more fluids of known density.

Equation 1 relates the natural frequency ($\omega$) of the vibrating tube to its mass.

$$\omega_u^2 = K_f/m$$

wherein $$\omega^2 = \omega_u^2 - \tfrac{1}{2}(C/m)^2 \qquad (1)$$

wherein $K_f$ is the force constant and m is the mass of the tube and contents, $\omega_u$ is the undamped natural frequency of the system. C is the damping constant for the system and $C/m$ is $\omega_u/Q$ where Q is proportional to the sharpness of the resonance frequency. In the ideal case, where Q is large, the resonance frequency is essentially $\omega_u$.

The difference in density between a test fluid and a reference fluid in the vibrating tube is related to the difference in mass of the system in these two cases, since the interior volume ($v_I$) of the tube is contant. Thus, one obtains $$\frac{m - m_o}{v_I} = \frac{K_f}{v_I}\left[\frac{1}{\omega^2} - \frac{1}{\omega_o^2}\right] = d - d_0 \qquad (2)$$

where the zero subscript refers to the reference fluid. In terms of the period of oscillation ($\tau$), $$(d-d_o) = K(\tau^2 - \tau_o^2) \qquad (3)$$

wherein $K = K_f/4\pi^2 v_I$. The calibration constant K can be determined from period measurements on two fluids of known density.

Art densimeters employing vibrating tubes employ a variety of means for vibrating the tube and sensing the induced vibration. Electrical means, which appear to be the more popular means, generally require the presence of electrical components such as insulated multi-turn electromagnetic coils or Piezo electric crystals adjacent to or on the tube. This has had the effect not only of complicating the devices but also limiting the conditions, especially temperature, under which they can be operated. For example, the devices of Kratky et al and Picker et al as described in Z. Angew, Phys. 27, 273 (1969) and in J. Solution Chem. 3 (5), 377 (1974) respectively, are limited, it appears, to operating temperatures below about 150° C.

Patentees have contributed many devices. Representative of these are, for example, Janssen who in U.S. Pat. No. 3,728,893 teaches torsional oscillation of a U-tube with electrical sensing; Kratky et al who in U.S. Pat. No. 4,170,128 teach a device comprising a U-shaped bending type oscillator connected with a tensioned body responsive to temperature and pressure; Brockhaus who in U.S. Pat. No. 3,456,491 teaches a device comprising a straight pipe in a variable magnetic field adapted to oscillate at resonant frequency; Agar who in U.S. Pat. No. 3,763,692 teaches a process for measuring the absolute density of a fluid using a pipe for the fluid and a bar of the same material as a standard; Abbotts who in U.S. Pat. Nos. 3,623,357 and 3,648,512 teaches densimeters for gases which oscillate a hollow cylinder in a bell-like manner; Catherall who in U.S. Pat. No. 3,955,401 teaches a densimeter tube and cantilevers vibrating in antiphase; Kratky et al who in U.S. Pat. No. 3,910,101 teaches a device comprising mechanical to electrical transducer, influenced by an oscillatory mass containing the test fluid, connected to an electrical to mechanical, transducer acting on the mass; Supanick who in U.S. Pat. No. 4,170,894 teaches a four-step method comprising measuring the pulse repetition frequency of an oscillator containing air or a test gas; Ghahramani who in U.S. Pat. No. 4,215,566 teaches a Piezo crystal for sensing frequency and Muramoto who in U.S. Pat. No. 4,132,110 teaches a Piezo crystal to excite oscillation or vibration.

It is apparent that there is a need for, and it is an object of this invention to provide, a simple vibrating tube type densimeter capable of operation under severe conditions such as elevated temperature.

SUMMARY OF THE INVENTION

A vibrating tube densimeter for fluids comprising:
a U-shaped tube adapted to contain test fluid;
electrical means for vibrating the tube in the magnetic field of a permanent magnet; and
electrical means for sensing the resonant frequency of the tube;
wherein the means for vibrating the tube and the means for sensing the vibration frequency of the tube comprise separate bare wire electrical conductors, each conductor passing once through said magnetic field, the conductors being insulatively attached to and adapted to move with said vibrating tube, whereby to permit operation up to about 500° C.

DESCRIPTION OF THE PREFERRED EMBODIMENTS

The invention is best illustrated by reference to the figures.

Figure 1:
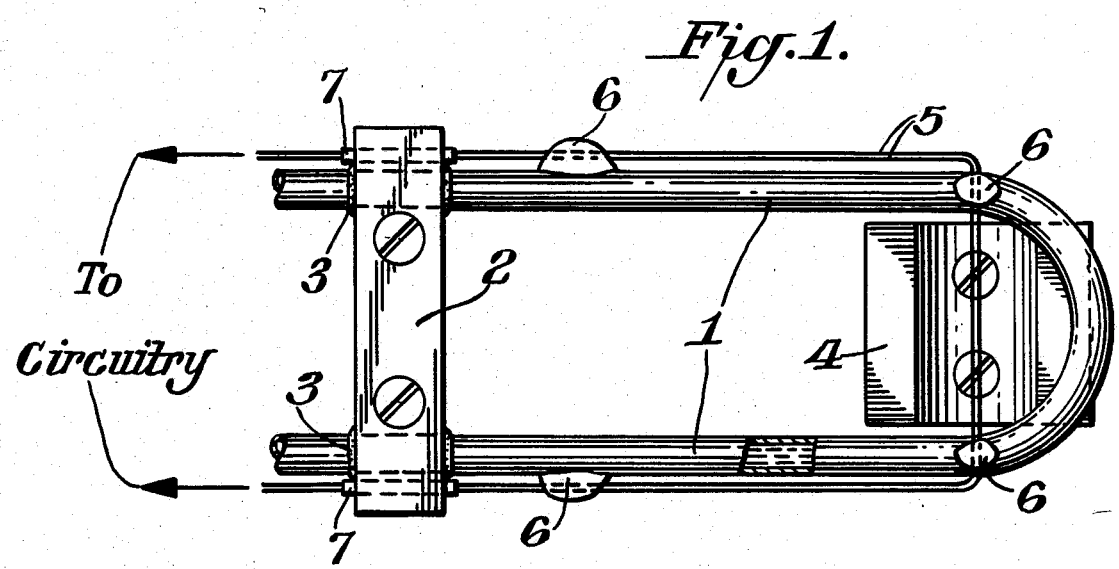
FIG. 1 is a plan view of a U-Tube of the invention provided according to the invention, with single electrical conductors, one of which vibrates the tube and the other senses the resultant vibration frequency, both by interaction with an essentially constant magnetic field in cooperation with circuitry shown in FIG. 3.

FIG. 1 shows a preferred arrangement of an invention U-tube with vibration and sensing means (sometimes called drive and pickup means). The, preferably nonmagnetic, U-tube 1 is fastened securely by any convenient means, into support 2 fabricated, for example, from brass. In this example, solder 3 is employed. The materials of construction and the dimensions of the tube are not critical to its function; the art worker will select materials and dimensions appropriate to the task. For high temperature work it was found convenient and practical to employ 24 cm long "Hastelloy" C-276 tube having an outside diameter of 1.5 mm and an inside diameter of 1.1 mm. The tube, restrained only at support 2, is free to vibrate in the direction normal to the plane of the drawing of FIG. 1. The preferred unsupported length is 6.4 cm. Although the tube is shown in the preferred U-shape, it is understood to be within the invention and within the ambit of claims to employ tubes having an A-shape and any desired unsupported length.

A permanent magnet 4 is installed below the apex of U-tube 1 where it provides an essentially constant magnetic field. It is this magnet which fixes the upper limit of temperature at which the invention device can be operated. For a device of the dimensions supra, a 60 g "Alnico V" magnet is preferred. Such magnets are operable up to at least about 500° C.

Figure 3:
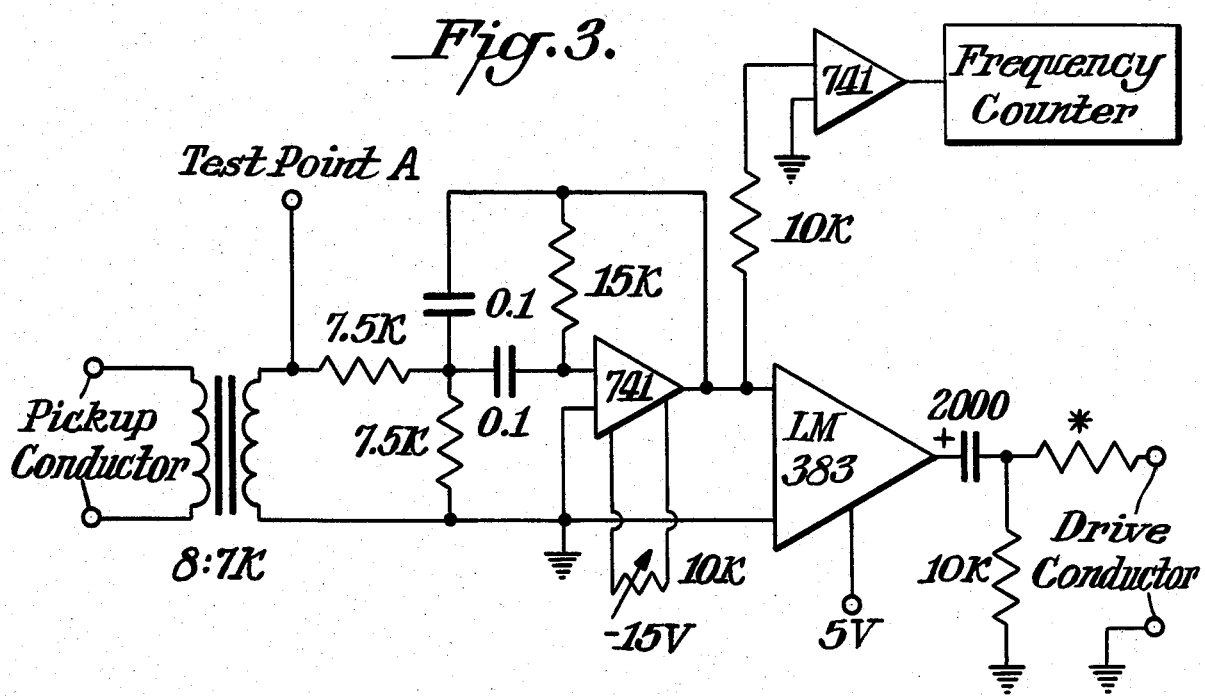
FIG. 3 is a schematic drawing of electric circuitry which cooperates with the conductors of FIGS. 1 and 2 to vibrate the tube and to sense the resultant vibration frequency.

Electrical conductors 5, by interaction with the magnetic field of magnet 4, in cooperation with the circuitry of FIG. 3 infra, provide for vibration of the tube and for sensing the frequency of the induced vibration. The relative positions of the conductors is not critical so long as they are placed perpendicular to both the magnetic field of magnet 4 and the motion of tube 1.

The conductors are normally bare commercial wire selected with a view to the conditions under which the device will be used. For very high temperature service, say to 500° C., 0.13 to 0.38 mm diameter "Constantan" wire is preferred. The conductors, in this embodiment, are held in place by commercial ceramic cement 6 capable of high temperature operation. The conductors pass out of the vibration region through insulating sleeve 7 in support 2, where they join the circuitry of FIG. 3.

Figure 2:
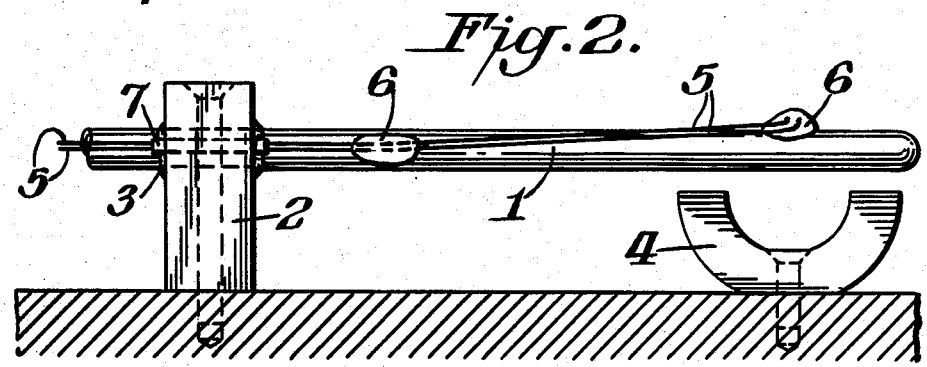
FIG. 2 is an elevation view of the device of FIG. 1.

FIG. 2 is an elevation view of the same device. The device of FIGS. 1 and 2 can be enclosed in a housing not shown, e.g., a machined alumunum block adapted to provide constant temperature to the vibrating U-tube.

The pickup and drive conductors are incorporated into the electronic circuit shown in FIG. 3. The circuit seeks the resonant frequency. The small voltage induced in the pickup conductor by its movement in the magnetic field is amplified by the transformer and fed to the first 741 operational amplifier which is configured as an active bandpass filter with a unity gain and peaking factor, centered about the resonant frequency whereby to reject electrical noise. The resultant signal is fed to the LM 383 amplifier which drives the drive conductor with a square wave 180° out of phase with the input signal. The current flowing through the drive conductor in the magnetic field in this fashion produces a stable oscillation of the vibrating tube at its resonant frequency. The resistor in series with the drive wire (denoted by an asterisk) is adjusted to provide 0.01–0.02 volts peak to peak at test point A. It limits the power dissipated in the drive wire to less than 10 milliwatts. The second 741 operational amplifier is used to amplify the signal before being monitored, using a frequency counter with 1 microsecond resolution. Since the period of oscillation is ca. 5000 microseconds, the required precision on the period measurement of a few parts in $10^7$ is obtained by averaging over $10^4$ periods.

The procedure for using the invention device is essentially that employed with art devices. In outline, the usual procedure consists first in determining the values of the calibration constant K of equation (3) supra using two fluids of known density such as water and nitrogen. Under selected pressure and temperature conditions, the resonant frequency of the loaded tube is measured for the two fluids. The value of K is calculated by substitution on the measured or observed periods into equation (3).

The instrument was tested with sodium chloride solutions of various concentrations, at several temperatures and pressure inter alia, resulting in close agreement with reliable art values.

The use of bare wire conductors vice insulated conductors as is conventional in coils, lies at the heart of this invention and permits service at temperatures well above those to which conventional coils are limited because of decomposition of the insulation.

That which is claimed is:

1. In a vibrating tube densimeter for fluids comprising:
   a U-shaped tube adapted to contain test fluid;
   electrical means for vibrating the tube in a magnetic field; and
   electrical means for sensing the resonant frequency of the tube;
   the improvement wherein the means for vibrating the tube and the means for sensing the resonant frequency of the tube comprise separate bare wire electrical conductors, each conductor passing once through said magnetic field, the conductors being insulatively attached to and adapted to move with the vibrating tube, whereby to permit operation up to about 500° C.

* * * * *